United States Patent
Galesso et al.

(10) Patent No.: US 12,403,646 B2
(45) Date of Patent: Sep. 2, 2025

(54) METHOD FOR 3D PRINTING WITH A BIO-INK

(71) Applicant: FIDIA FARMACEUTICI S.p.A., Abano Terme (IT)

(72) Inventors: Devis Galesso, Abano Terme (IT); Riccardo Beninatto, Abano Terme (IT); Mauro Pavan, Abano Terme (IT); Alba Di Lucia, Abano Terme (IT)

(73) Assignee: FIDIA FARMACEUTICI S.p.A., Abano Terme (IT)

(*) Notice: Subject to any disclaimer, the term of this patent is extended or adjusted under 35 U.S.C. 154(b) by 0 days.

(21) Appl. No.: 17/909,787

(22) PCT Filed: Mar. 16, 2021

(86) PCT No.: PCT/IB2021/052160
§ 371 (c)(1),
(2) Date: Sep. 7, 2022

(87) PCT Pub. No.: WO2021/186335
PCT Pub. Date: Sep. 23, 2021

(65) Prior Publication Data
US 2024/0217166 A1    Jul. 4, 2024

(30) Foreign Application Priority Data

Mar. 17, 2020    (IT) ........................ 102020000005692

(51) Int. Cl.
*B29C 64/106*    (2017.01)
*B33Y 10/00*    (2015.01)
(Continued)

(52) U.S. Cl.
CPC ............ *B29C 64/106* (2017.08); *B33Y 10/00* (2014.12); *C07K 14/78* (2013.01); *C08B 37/006* (2013.01);
(Continued)

(58) Field of Classification Search
None
See application file for complete search history.

(56) References Cited

U.S. PATENT DOCUMENTS 5,676,964 A * 10/1997 Della Valle ........... A61L 31/042
536/55
7,863,256 B2 * 1/2011 Schiavinato ......... A61K 31/728
536/53
(Continued)

FOREIGN PATENT DOCUMENTS

WO    WO 2014/122580 A1    8/2014

OTHER PUBLICATIONS

Hölzl, Katja, et al. "Bioink properties before, during and after 3D bioprinting." Biofabrication 8.3 (Sep. 23, 2016): 032002. (Year: 2016).*
(Continued)

*Primary Examiner* — Benjamin A Schiffman
(74) *Attorney, Agent, or Firm* — Birch, Stewart, Kolasch & Birch, LLP

(57) ABSTRACT

A bio-ink for use in 3D printing, the related conjugate and the preparation process of an intermediate consisting of a bifunctional photoreactive linker are described. Said bio-inks are used for the manufacturing of constructs by 3D printing.

6 Claims, 4 Drawing Sheets

(51) Int. Cl.
  *C07K 14/78* (2006.01)
  *C08B 37/00* (2006.01)
  *C08B 37/08* (2006.01)
  *C08H 1/00* (2006.01)
  *C08L 5/08* (2006.01)
  *C08L 89/06* (2006.01)
  *B33Y 70/00* (2020.01)
  *B33Y 70/10* (2020.01)

(52) U.S. Cl.
  CPC ........... *C08B 37/0072* (2013.01); *C08H 1/00* (2013.01); *C08L 5/08* (2013.01); *C08L 89/06* (2013.01); *B33Y 70/00* (2014.12); *B33Y 70/10* (2020.01)

(56) References Cited

U.S. PATENT DOCUMENTS

| | | | | |
|---|---|---|---|---|
| 7,884,087 | B1* | 2/2011 | Bellini | A61K 47/61 424/443 |
| 8,512,752 | B2* | 8/2013 | Crescenzi | C08B 37/0072 424/422 |
| 8,846,640 | B2* | 9/2014 | D'este | C08B 37/0003 514/54 |
| 9,889,226 | B2* | 2/2018 | Campisi | A61L 27/20 |
| 10,533,061 | B2* | 1/2020 | Boiteau | A61Q 19/00 |
| 2005/0058703 | A1* | 3/2005 | Chang | A61K 9/4825 424/456 |
| 2013/0172985 | A1* | 7/2013 | Prestwich | A61L 27/222 435/177 |

OTHER PUBLICATIONS

Yin, Jun, et al. "3D bioprinting of low-concentration cell-laden gelatin methacrylate (GelMA) bioinks with a two-step cross-linking strategy." ACS applied materials & interfaces 10.8 (Feb. 6, 2018): 6849-6857. (Year: 2018).*

Beninatto et al., "Photocrosslinked hydrogels from coumarin derivatives of hyaluronic acid for tissue engineering applications", Materials Science & Engineering C, 2019, vol. 96, pp. 625-634.

International Search Report, issued in PCT/IB2021/052160, dated Jun. 24, 2021.

Ouyang et al., "30 Printing of Shear-Thinning Hyaluronic Acid Hydrogels with Secondary Cross-Linking", ACS Biomater Sci Eng, 2016, vol. 2, pp. 1743-1751.

Written Opinion of the International Searching Authority, issued in PCT/IB2021/052160, dated Jun. 24, 2021.

* cited by examiner

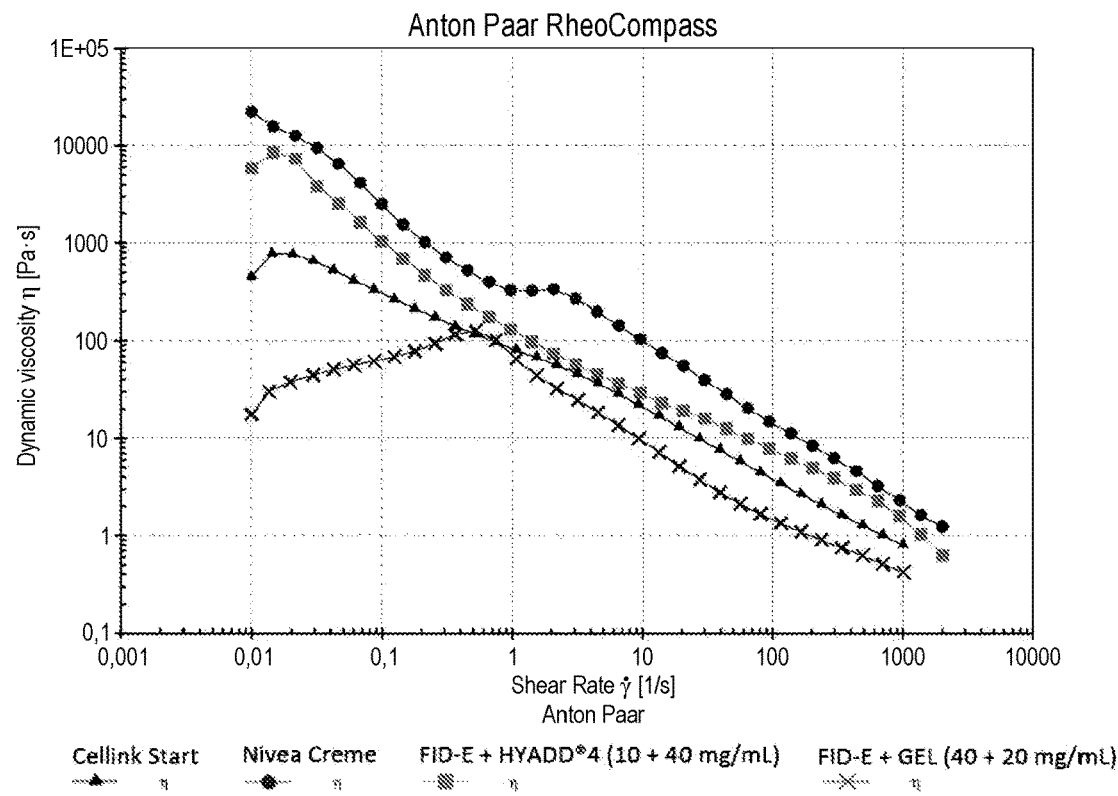
Figure 1: measure of dynamic viscosity $\eta$
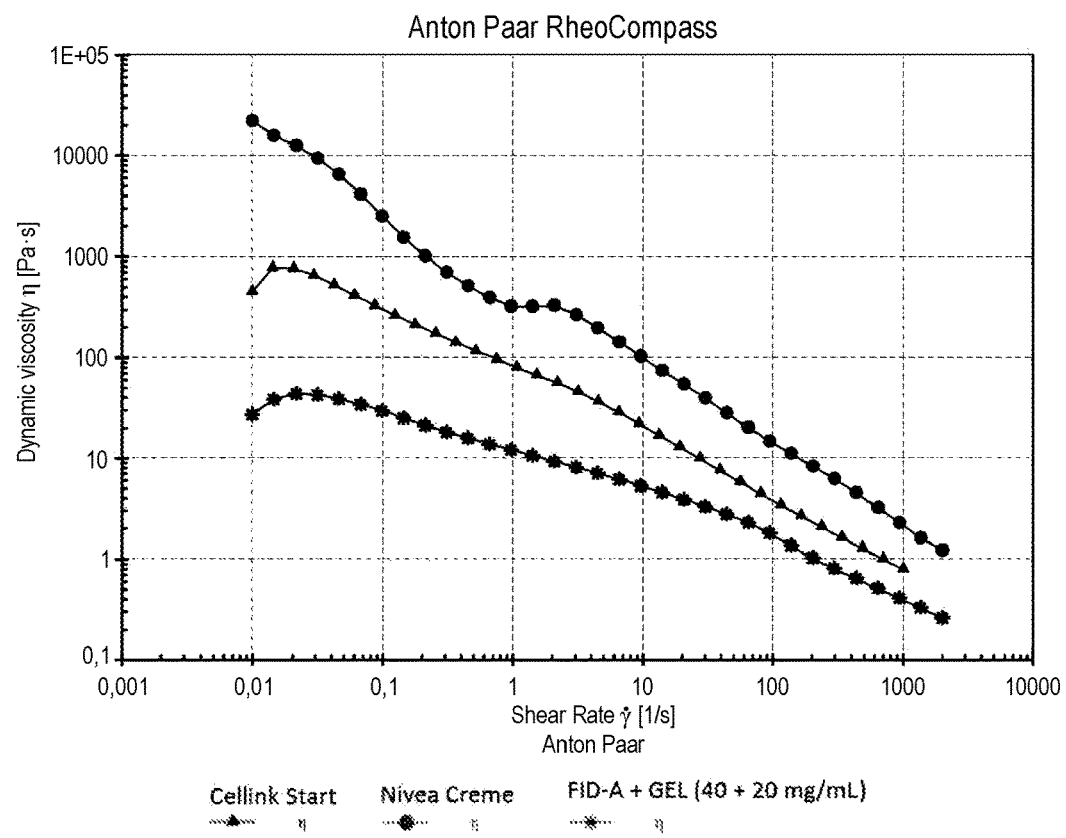
Figure 2: measure of dynamic viscosity $\eta$

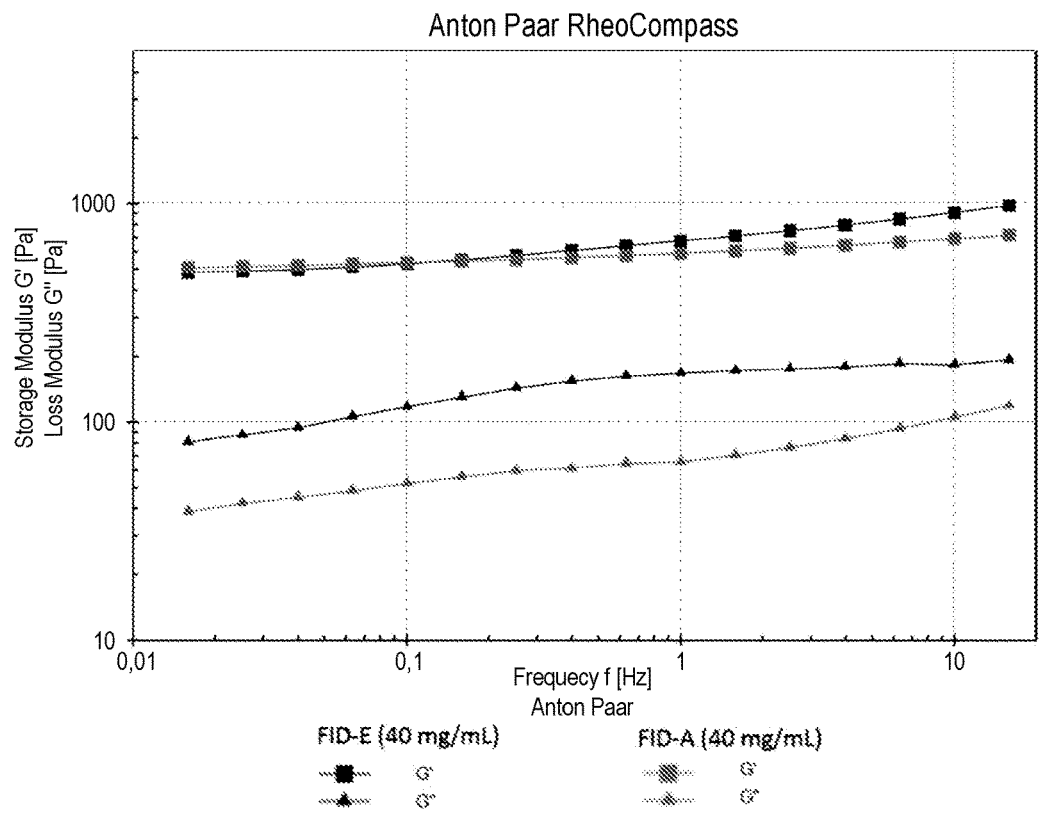
Figure 3: evaluation of viscous and elastic moduli (G'; G'')
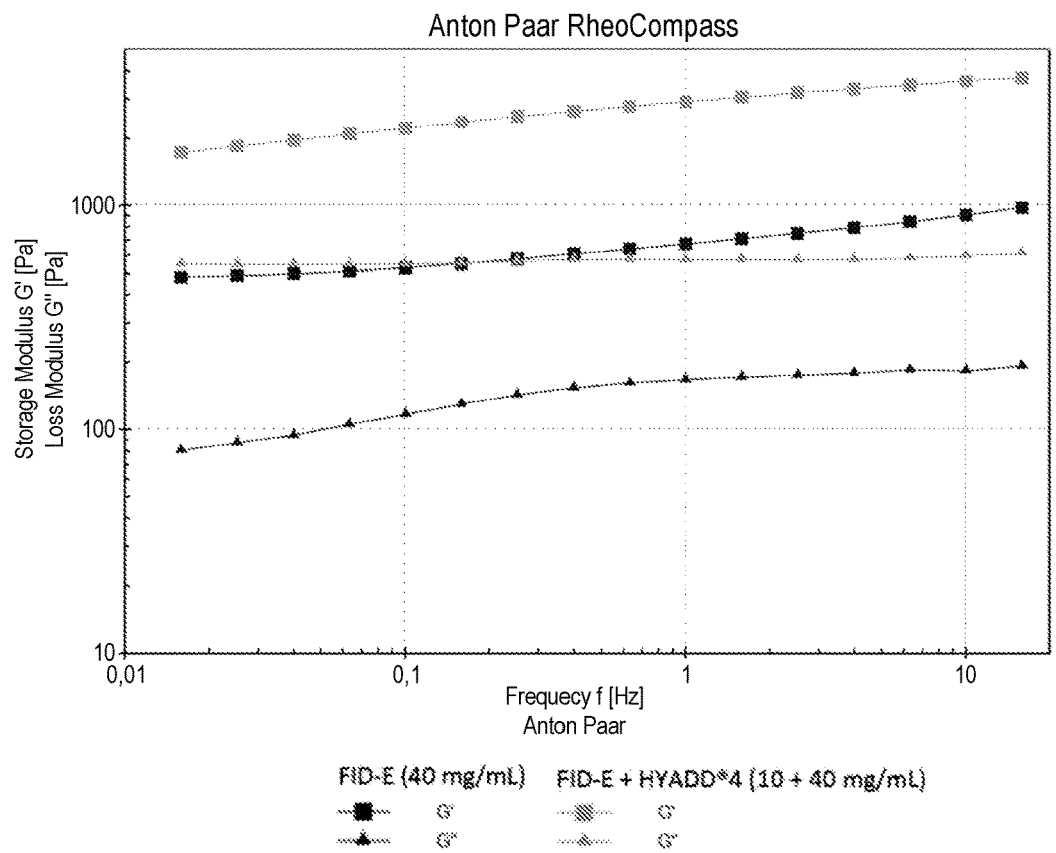
Figure 4: evaluation of viscous and elastic moduli (G'; G'')

METHOD FOR 3D PRINTING WITH A BIO-INK

BACKGROUND OF THE INVENTION

(1) Field of the Invention

The present invention describes a use of a bio-ink for 3D printing, a related intermediate conjugate and the preparation process of an intermediate consisting of a photoreactive linker.

An object of the present invention is the use of a bio-ink for 3D printing, i.e. of an ink to be used both in the 3D-printing field and in the 3D-bioprinting field, said bio-ink comprising a photocrosslinkable conjugate of hyaluronic acid and bifunctional photoreactive linker, or a photocrosslinkable conjugate of gelatin and bifunctional photoreactive linker, or mixtures of the two conjugates, photocrosslinkable.

Further object of the invention is a conjugate of gelatin and a bifunctional photoreactive linker, said linker consisting of umbelliferone and a triethylene glycol spacer bound through an ether bond, said conjugate being crosslinkable.

Further object of the present invention is a preparation process of a bifunctional photoreactive linker consisting of umbelliferone bound through an ether bond:
  to a triethylene glycol chain, or
  to a linear C4-C20 alkyl chain, preferably a C8-C16 alkyl chain, even more preferably an octyl chain or a dodecyl chain,
such linker being capable of binding to HA or gelatin through the formation of an amide bond and thus forming the HA conjugate or the gelatin conjugate, photocrosslinkable, said process comprising the following steps:
  i) etherification of the umbelliferone with N-BOC-2-[(2-p-tosyloxyethoxy)ethoxy]ethylamine or with 8-((tert-butoxycarbonyl) amino)(C4-C20 alkyl) 4-methylbenzenesulfonate, in the presence of acetone and potassium carbonate;
  i) deprotection reaction of the amine group at room temperature.

(2) Description of Related Art

One of the most interesting fields for tissue and organ damage repair certainly is the so-called tissue engineering, whose aim is substantially to create constructs (scaffold) to be applied in various injuries, in order to promote the original tissue regeneration or entirely replacing a damaged organ.

In the regenerative process, the constructs can host the cells present in the injury site, which will colonize it, or they can contain cells inserted during the step of construct's preparation, with the function of activating, stimulating and improving the regenerative process, determining the injury closure or organ integration. Such constructs must naturally have some essential characteristics: they must be completely free of toxicity; they must be biocompatible; they must have mechanical characteristics of strength and elasticity suitable for the implant site; they must be capable of guaranteeing cell viability, proliferation and organization, both when it comes to cells present in the implant site, and when cells are encapsulated in the biomaterial at the manufacturing step, mixing them to the hydrogel.

Therefore, the tissue engineering summarizes typically biological aspects with other certainly engineering aspects, also considering that the tissues have deeply different biological, biochemical, mechanical characteristics: the bone is very different from the skin, the liver from the blood vessel.

A determined pulse to the tissue engineering field was given by the technological development of the three-dimensional printing (3D-printing): it is a matter of a set of technologies capable of generating physical model from a digital information. In brief, a particular printer converts a low-viscosity polymer "ink" (ink) into a three-dimensional solid structure which is perfectly identical to an anatomic model, according to the instruction provided by a suitably-programmed computer.

The ink solidification generally occurs by irradiation as it is gradually delivered (extruded) from the printer: through light-induced polymerization reactions, the ink crosslinks i.e. polymerizes, transforming into a solid having exactly the predetermined form. If it is desirable that the final construct contains cells, it is necessary that they are mixed with the ink (encapsulated) before the extrusion phase: the ink must obviously guarantee viability and the proliferability of cellular material contained therein. In this case it is more correct to say 3D-bioprinting and the ink is defined as bio-ink.

In the medical and surgical field, it is certainly very useful being able to have anatomic models customized for each patient, being these intended to repair a tissue or even to replace an entire organ.

The structures that can be obtained following these techniques are also particularly suitable for the release of the active substances included in the construct and for the creation of matrices on which testing new drugs, contributing thus to their faster development, less invasive, less expensive and ethically correct.

A determining factor for the preparation of the described structures is the ink type that, because of the fact of giving rise to scaffolds with very peculiar characteristics, must have specific requirements both from the technical point of view (for example, easy processing) and from the biological point of view, such as biocompatibility and very low or no toxicity.

To date, the more common inks known to the skilled person consist substantially of biocompatible polymers among which there are gelatin, hyaluronic acid, fibroin, alginate, cellulose, variously modified and/or mixed each other.

For example, WO2011088213 describes inks formed by hyaluronic acid and gelatin, derivatized with methacrylic anhydride and photopolymerized with UV light in the presence of a photoinitiator; Hölzl K et al. (Biofabrication 2016, 8(3):032002) describes an ink based on hyaluronic acid esterified with pentenoic anhydride polymerizing in the presence of a specific photoinitiator; Yin J. (ACS Appl. Mater. Interfaces 2018, 10, 6849-6857) describes the features of methacrylate-crosslinked gelatin-based inks, further mixed to gelatin in order to improve its printability.

In general, in the state of the art, regardless of the polymer used, the polymerization occurs through the use of a photoinitiator, which is potentially toxic, as the methacrylate is, which is used for the chemical modification of the starting polymer.

Therefore, an objective of the present invention is to identify inks overcoming the drawbacks of the inks according to the state of the art.

In fact, the inks object of the use according to the present invention do not involve the use of photoinitiators and do not use toxic substances for the derivatization of the starting polymer, thus giving rise to materials with a very high safety profile, both when used as such and when also containing cellular material.

They are also provided with all the functional, rheological and mechanical features, which make them suitable for being used both in the 3D-printing and in the 3D-bioprinting; that is why, and for simplicity, the inks described in the present invention are always defined as bio-ink or bioink, even when not containing cells.

BRIEF DESCRIPTION OF THE DRAWINGS

FIG. 1 is a graph showing dynamic viscosity versus shear rate as set forth in Example 7.

FIG. 2 is another graph showing dynamic viscosity versus shear rate as set forth in Example 7.

FIG. 3 is a graph showing the evaluation of viscous and elastic moduli as set forth in Example 7.

FIG. 4 is another graph showing the evaluation of viscous and elastic moduli as set forth in Example 7.

DETAILED DESCRIPTION OF THE INVENTION

Figure 5:
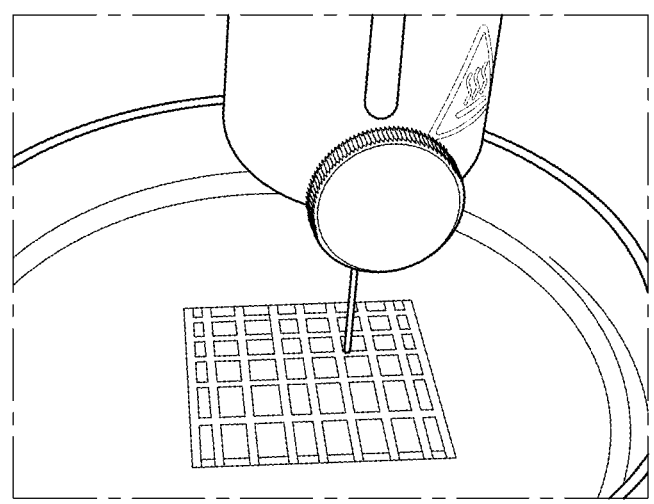
FIG. 5 illustrates the deposition of the first layer as set forth in Example 7.
Figure 6:
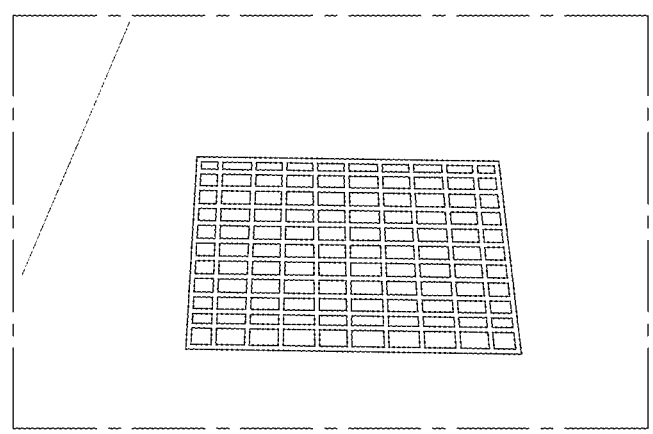
FIG. 6 illustrates crosslinking by irradiation at 365 nm as set forth in Example 7.

An object of the present invention is the use of a bio-ink for 3D printing, i.e. the use of an ink to be used both in the 3D-printing field and in the 3D-bioprinting field, said bio-ink comprising a photocrosslinkable conjugate of hyaluronic acid and bifunctional photoreactive linker, or a photocrosslinkable conjugate of gelatin and bifunctional photoreactive linker, or mixtures of the two photocrosslinkable conjugates.

Further object of the invention is a conjugate of gelatin and a bifunctional photoreactive linker bound through an amide bond, said linker consisting of umbelliferone and a triethylene glycol spacer bound through an ether bond, said conjugate being crosslinkable and having the structure of formula (III)

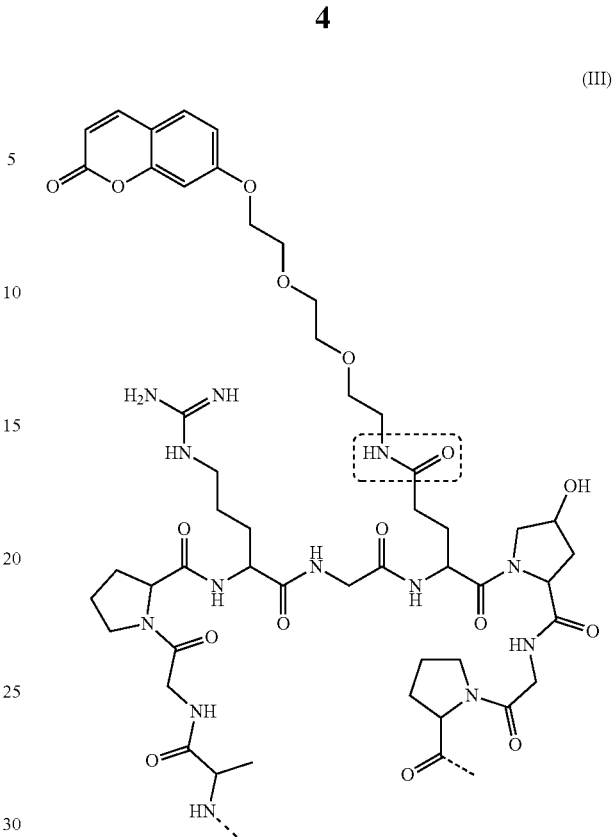

(III)

Further object of the present invention is a preparation process of a bifunctional photoreactive linker consisting of umbelliferone bound through an ether bond:
- to a triethylene glycol chain, or
- to a linear C4-C20 alkyl chain, preferably a C8-C16 alkyl chain, even more preferably an octyl chain or a dodecyl chain, such linker being capable of binding to HA or a gelatin through the formation of an amide bond and thus forming the HA conjugate or the gelatin conjugate, photocrosslinkable, said process comprising the following steps:
  i) etherification of the umbelliferone with N-BOC-2-[(2-p-tosyloxyethoxy)ethoxy]ethylamine or with 8-((tert-butoxycarbonyl)amino)(C4-C20 alkyl) 4-methylbenzenesulfonate, in the presence of acetone and potassium carbonate;
  ii) deprotection reaction of the amine group at room temperature.

Therefore, the present invention relates to the use of a bio-ink (bioink) to be used in the 3D-printing field and in the 3D-bioprinting field, said bio-ink comprising a conjugate of hyaluronic acid photocrosslinkable or a photocrosslinkable gelatin conjugate or photocrosslinkable mixtures thereof, having the following features:
- total biocompatibility;
- capability of adhering cells present in the implant site, and allow them to subsequently proliferate;
- capability of encapsulating cells in the pre-polymerization step, maintaining intact their post-polymerization viability;
- low viscosity pre-polymerization at temperature lower than the body temperature, so as to allow a good extrusion in the printing step, with or without cellular material within;

a combination of viscosity and yield stress (tangential stress value below which the material is static) capable of allowing the material extrusion and maintaining the shape after the extrusion for a time sufficient for the crosslinking to be performed;

sterilizability; the bio-inks according to the present invention can be sterilized through filtration by 0.45μ filters and/or heat treatment in autoclave;

high polymerization rate, so as to reduce UV-light exposure time; such features being highly desirable, especially when the bio-ink contains cells;

suitable rheological-mechanical characteristics post-polymerization, which are different depending on the specific scope of application.

The bio-inks for use according to the present invention are also prepared by a process using low toxicity and dangerousness reactants (not flammable, not explosive) and the crosslinking is performed without using any photoinitiator.

Among the various polymers known, gelatin and hyaluronic acid (HA) are particularly indicated for the purposes of the present invention, which are made photocrosslinkable by conjugation with a bifunctional photoreactive linker, that, when exposed to the UV light of a precise wavelength, induces the polymerization through crosslinking, and then bio-ink solidification, without the necessity to use a photoinitiator.

The bifunctional photoreactive linker (that for the sake of brevity is defined as "linker") used according to the present invention is a coumarin linker, i.e. consisting of an umbelliferone residue, bound to a spacer, where the spacer can be a polyethylene glycol, in particular triethylene glycol (TEG), or a linear C4-C20 alkyl chain, preferably a C8-C16 alkyl chain, even more preferably an octyl chain or a dodecyl chain.

The bifunctional photoreactive linker TEG-Umbelliferone is represented by the following formula (I):

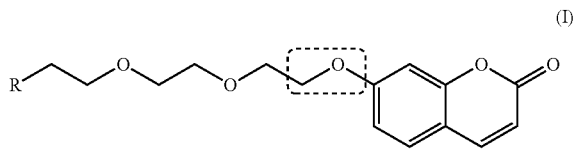

(I)

where:

R=—NH$_2$ for the formation of an amide bond;

R=—I for the formation of an ester bond.

The bifunctional photoreactive linker alkyl chain-Umbelliferone is represented by the following formula (II):

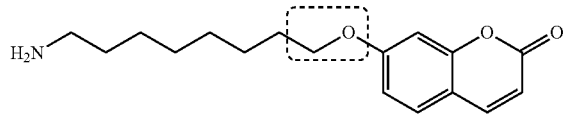

(II)

Therefore, the spacer, whatever it is, at one end it always binds the umbelliferone through an ether bond and at the other end it binds to the selected polymer, i.e. HA or gelatin. The spacer is suitably functionalized in connection with the ester or amide bond-type to be created with the polymer. More precisely:

the bond between the umbelliferone-polyethylene glycol linker and HA can be an ester or amide bond;

the bond between the umbelliferone-alkyl linker and HA is exclusively amidic;

the bond between the linker, umbelliferone-polyethylene glycol or umbelliferone-alkyl, and gelatin is always amidic.

Gelatin is the product of collagen denaturation, it is soluble in water in which it creates viscous solutions, and it is recognized as GRAS (Generally Recognized As Safe) by the U.S. regulatory agency FDA.

It is widely used in the food, pharmaceutical, cosmetic, and nutraceutical industry, within food supplements for the skin, hair and joint health. Compared to the collagen from which it is produced, gelatin is much less immunogenic, but it preserves RGD domains (amino acid sequence Arginine-Glycine-Aspartic Acid), providing a stimulation effect on cell migration, proliferation and differentiation, and the attack sites for the degradation by MMPs (Matrix metalloproteinases), which make it enzymatically-degradable.

The gelatin preferably used in the present invention is type-B bovine-origin (i.e. obtained by basic hydrolysis of collagen) and has about 225 g Bloom (gelling capability after cooling, measured in accordance with USP XX (1990) 1017).

The photocrosslinkable gelatin conjugate is obtained by conjugation of carboxyl groups of gelatin by amidation with a bifunctional photoreactive linker, consisting of an umbelliferone residue bound to a polyethylene glycol spacer, preferably triethylene glycol, or a linear C4-C20 alkyl chain, preferably a C8-C16 alkyl chain, even more preferably an octyl chain or a dodecyl chain.

More preferably, the gelatin photocrosslinkable conjugate is obtained by conjugation of carboxyl groups of gelatin by amidation with a bifunctional photoreactive linker, consisting of an umbelliferone residue bound to a triethylene glycol spacer.

It is then conjugated with the photoreactive linker as described above, preferably with the linker TEG-umbelliferone, through the formation of an amide bond involving the carboxyl groups of gelatin and the spacer suitably functionalized, obtaining the conjugate of formula (III) showed below (III)

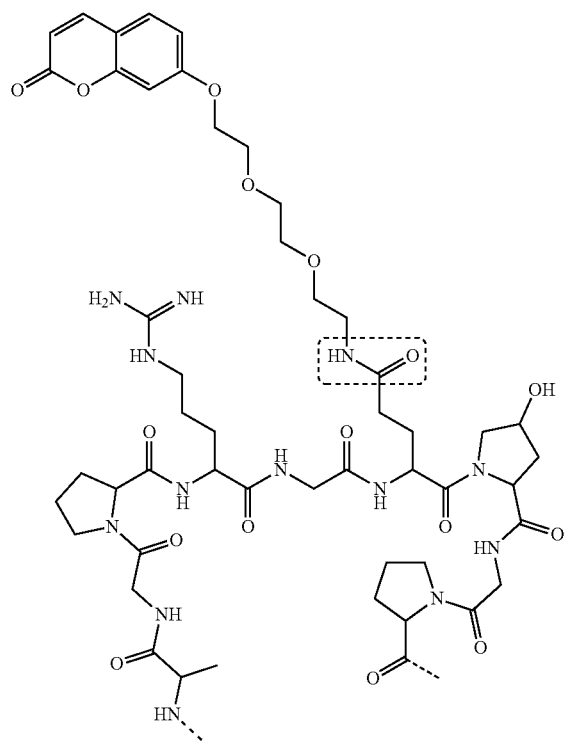

Hyaluronic acid is a hetero-polysaccharide composed by alternating residues of D-glucuronic acid and N-acetyl-D-glucosamine, straight-chain, with a molecular weight which can range between 400 and $3\times10^6$ Da, depending on the extraction source or the preparation method used. HA is present in each area of the biological organism, and it is involved in many processes relating to the mechanical support of cells of many tissues such as skin, tendons, muscles and cartilage. HA is decisive in the tissue repair process both from the structural point of view and as substance stimulating a wide series of processes wherein it is directly or indirectly involved (Weigel P. et al., *J Theoretical Biol*, 1986:219-234; Abatangelo G. et al., *J Surg Res*, 1983, 35:410-416; Goa K. et al., Drugs, 1994, 47:536-566). Furthermore, HA is provided with anti-inflammatory activity, since it modulates cytokine release, in particular IL-1, and it has an analgesic activity, since it binds to opioid specific receptors.

From the chemical point of view, the HA molecule is provided with numerous functional groups which make it variably modifiable, for example by salification with organic or inorganic bases, by esterification with alcohols of various nature, by amidation with not therapeutically active amines.

The starting hyaluronic acid for preparing bioink or bioinks described herein can be produced and purified according to the known method, for example, by extraction from cockscombs (EP138572), by fermentation from *Streptococcus* (WO2018020458; WO2019016699), by biosynthesis from *Bacillus* (WO2012032154). HA produced and purified from *Streptococcus* or *Bacillus*, more preferably from *Streptococcus* is preferred, with a weight average MW comprised between 100,000 and 250,000 Da, preferably between 180,000 and 230,000 Da, for the sake of brevity defined as "MW 200 kDa", or HA with a weight average MW comprised between 500,000 and 730,000 Da.

Average molecular weight (MW) means the weight average MW calculated by the "intrinsic viscosity" method (Terbojevich et al., Carbohydr Res, 1986, 363-377).

Within the scope of the present invention, the conjugates of interest are obtained by esterification or amidation of the HA carboxyl group with a bifunctional photoreactive linker as described above, preferably consisting of triethylene glycol bound to umbelliferone, obtaining the conjugates of formula (IV) and (V) showed below:

HA-TEG-Umbelliferone Ester (IV)

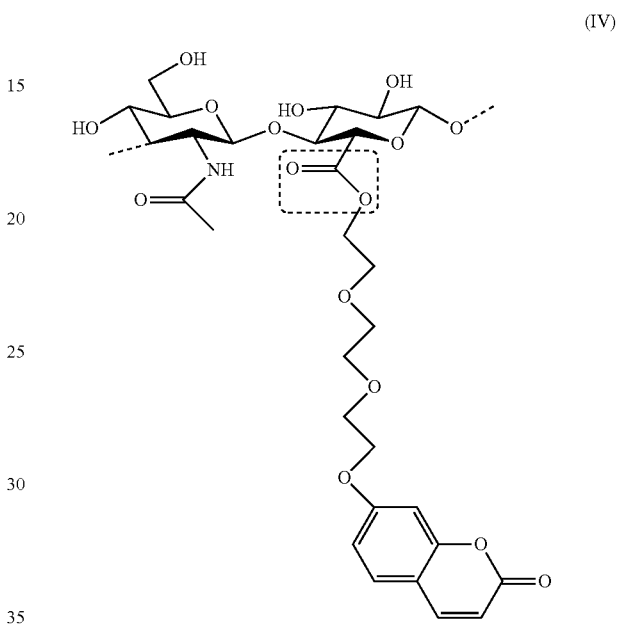

HA-TEG-Umbelliferone Amide (V)

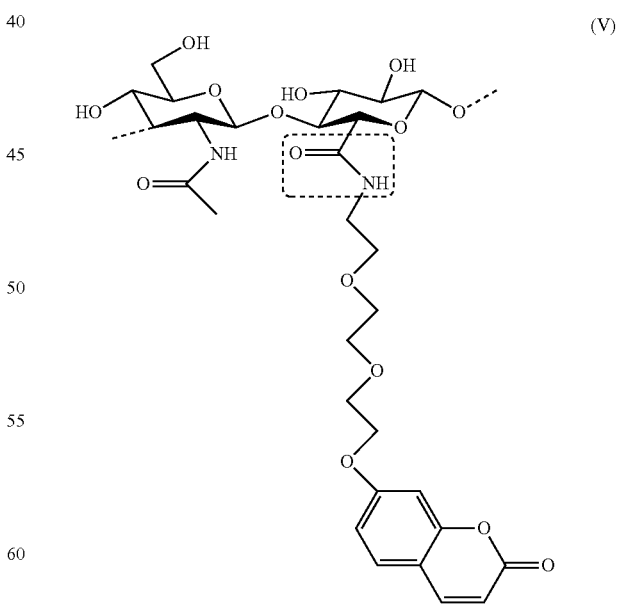

The HA-bifunctional photoreactive linker bond originates, after the polymerization by crosslinking, materials having a different degree of degradability depending on it deals with an ester (more degradable) or amide (less degradable) bond, however maintaining intact the characteristics of biocompatibility and non-toxicity.

The photocrosslinkable conjugate of hyaluronic acid is obtained by conjugation of the hyaluronic acid carboxyl group by esterification or amidation with a bifunctional photoreactive linker, consisting of an umbelliferone residue bound to a polyethylene glycol spacer, preferably triethylene glycol, or a linear C4-C20 alkyl chain, preferably a C8-C16 alkyl chain, even more preferably an octyl chain or a dodecyl chain.

More preferably, said photocrosslinkable conjugate of hyaluronic acid is obtained by conjugation of the hyaluronic acid carboxyl group by amidation with a bifunctional photoreactive linker, consisting of umbelliferone bound to a triethylene glycol spacer; even more preferably the starting hyaluronic acid is prepared and purified from *Streptococcus* (WO2018020458; WO2019016699) and has a weight average MW comprised between 100,000 and 250,000 Da, preferably between 180,000 and 230,000 Da.

Such derivatives are already known to the skilled person: WO2014122580 describes the synthesis thereof and claims the capability of forming "shape memory" sponges or hydrogels, i.e. very resistant, compact and capable of maintaining their shape also after cut, torsion and handling.

Within the scope of the present invention, it is demonstrated that such derivatives, normally used in the treatment of osteoarthritis and cartilaginous injuries, in the prevention of the post-surgical adhesions, soft tissue filling and deep and cavitated injuries, are suitable for the use as bio-ink for the manufacturing of constructs by 3D printing.

An object of the present invention is also therefore the use of the bio-inks described herein for the manufacturing of constructs by 3D printing.

The Applicant has also developed a new preparation process of the bifunctional photoreactive linker, suitable for the formation of a subsequent amide bond which, with respect to that described in WO2014122580, uses non-toxic and not-flammable reactants, is more rapid, cheaper, globally more safe and industrially more convenient.

The present invention also refers to a preparation process of a bifunctional photoreactive linker consisting of umbelliferone bound through an ether bond:
  to a triethylene glycol chain (TEG), or
  to a linear C4-C20 alkyl chain, preferably a C8-C16 alkyl chain, even more preferably an octyl chain or a dodecyl chain,
such linker being capable of binding to HA or a gelatin through the formation of an amide bond and thus forming the HA conjugate or the gelatin conjugate, photocrosslinkable, said process comprising the following steps:
  i) etherification of the umbelliferone with N-BOC-2-[(2-p-tosyloxyethoxy)ethoxy]ethylamine or with 8-((tert-butoxycarbonyl)amino)(C4-C20 alkyl) 4-methylbenzenesulfonate, in the presence of acetone and potassium carbonate;
  i) deprotection reaction of the amine group at room temperature.

Briefly, the above-mentioned process involves only two distinct steps: initially the etherification step wherein the umbelliferone is bound to a reactant N-BOC 2-[(2-p-tosyloxyethoxy)ethoxy]ethylamine or 8-((tert-butoxycarbonyl) amino) (C4-C20 alkyl) 4-methylbenzenesulfonate, preferably 8-((tert-butoxycarbonyl)amino)octyl 4-methylbenzenesulfonate (marketed by Ambeed) through a rapid and clean reaction which involves the use of acetone as reflux solvent and potassium carbonate as base.

Then, the amine group is deprotected in a time comprised between 1 and 6 hours, at room temperature, providing the desired product (Umbelliferone-TEG-$NH_2$ or Umbelliferone-C4-C20-alkyl-$NH_2$) with a quantitative yield, without the necessity of further purification.

With respect to what is described in WO2014122580, the above-described process has numerous advantages:
The synthesis is more rapid and cheaper, thus requiring only two steps instead of the five steps expected in WO'580. Furthermore, a considerably lower amount of solvent is used; the use of sodium azide is avoided, that causes a high chemical risk; a hydrogenation involving the use of Pd/C (Palladium/Carbon) as catalyst is avoided; Palladium, due to its potential toxicity, must also be disposed as special waste.

The bio-ink for the use according to the present invention, both when consisting of HA conjugate or gelatin conjugate and when consisting of a mixture of the above-mentioned conjugates, can optionally be further mixed with cellular material, such as, for example, cells of connective, bone, cartilaginous, muscular tissue or mesenchymal cells and/or with further components selected from the following hyaluronic acid derivatives known in the state of the art, such as:
  amide derivatives described in EP1095064 and EP1853279. The aliphatic amide derivatives are preferred, in particular the hexadecyl amide prepared from a HA having a weight average molecular weight comprised between 500 kDa and 730 kDa, and having an average degree of amidation comprised between 0.1% and 10% molar, preferably comprised between 1% and 3% molar, detected by HPLC after amide hydrolysis and conjugation of the leaving exadecylamine with a fluorophore substance. The hexadecyl amide having the above-mentioned characteristics and an average derivatization degree comprised between 1% and 3% molar is described in EP1853279 and it is available under the trade name HYADD®-4;
  self-crosslinked internal esters with an esterification percentage not higher than 20%, preferably between 0.05 and 10%, as described in EP 0341745 and known to the state of the art as ACP®;
  crosslinked derivatives, obtained by the use of crosslinking agents such as BDDE (1,4-Butanediol diglycil ether), with a derivatization degree between 2.5 and 25% molar, preferably between 5 and 15% molar with respect to the hyaluronic acid repeating unit, and prepared from HA with a weight average MW comprised between 500 and 730 kDa, as described in EP2470230, and know under the name HBC.

The mixing with the further derivatives of HA increases and makes adjustable the rheological characteristics of the bio-ink and increases its resistance to the degradation action of hyaluronidases (Pavan 2016), thus making them suitable for any type of application.

Preferably, the bio-ink can comprise as further HA derivative
  amides described in EP1095064 and EP1853279, preferably hexadecyl amide prepared from a HA with a weight average molecular weight comprised between 500 kDa and 730 kDa, and having an average degree of amidation comprised between 0.1% and 10% molar, preferably comprised between 1% and 3% molar (HYADD®-4);
  self-crosslinked internal esters with an esterification percentage not higher than 20%, preferably between 0.05 and 10%, as described in EP 0341745 (ACP®);

crosslinked obtained by using crosslinking agents such as BDDE (1,4-Butanediol diglycil ether), with a derivatization degree between 2.5 and 25% molar, preferably between 5 and 15% molar with respect to the hyaluronic acid repeating unit, and prepared from HA having a weight average MW comprised between 500 and 730 kDa, prepared as described in EP2470230 (HBC).

Even more preferably, the bio-ink can comprise HYADD®-4 or HBC such as further HA derivative.

The bio-ink is prepared with variable concentrations of the polymers previously described, in connection with the result to be obtained, at the processing conditions, in the presence or not of cells within the bio-ink itself.

In particular, the bio-ink can comprise
- HA conjugate with the bifunctional photoreactive linker through ester or amide bond as previously described, at variable concentrations from 20 to 60 mg/mL, preferably comprised between 30 and 50 mg/mL, even more preferably equal to 40 mg/mL;
- gelatin conjugated with the bifunctional photoreactive linker through amide bond, at variable concentrations from 20 to 60 mg/mL, preferably comprised between 30 and 50 mg/mL, even more preferably equal to 40 mg/mL;
- mixtures of HA conjugate and gelatin conjugate, variably composed in connection with the material to be produced, the total concentration of the two components in mixture ranging from 30 to 80 mg/mL, preferably from 30 a 70 mg/mL, and more preferably being comprised between 30 and 60 mg/ml; preferably, with respect to the above-mentioned total concentration, the concentration of the gelatin conjugate ranging from 10 to 30 mg/mL, more preferably between 15 and 30 mg/mL, and even more preferably it is equal to 20 mg/mL;
- mixtures with HBC, HYADD®-4, ACP®: the additional polymer (selected from HBC, HYADD®-4, ACP®) is mixed in a ratio varying from 1:1 to 5:1, preferably from 3:1 to 4:1 with the HA conjugate or the gelatin conjugate. When the additional polymer is HBC, the preferred ratio is 1:1. The total concentration of the components forming the mixtures varies from 20 to 80 mg/mL, preferably from 40 to 70 mg/mL, more preferably from 40 to 60 mg/mL, and even more preferably from 40 to 50 mg/mL.

In exceptional cases, e.g. when specific rheological conditions are necessary and the additional polymer is selected from HYADD®-4 and ACP®, the ratio between the additional polymer and the HA conjugate or the gelatin conjugate can vary even from 1:1 to 1:2, preferably it is equal to 1:1.5.

In order to better illustrate the objective and the advantages of the present invention, some examples are provided, although they do not constitute in any way a limitation to the scope of the claims.

Example 1: Synthesis of the HA-TEG-Umbelliferone Conjugate Through Ester Bond from HATBA MW 200 kDa (as Reported in Ex. 9 WO2014122580)

Briefly, in a glass reactor equipped with a thermostatable glycol jacket and magnetic stirring, 2.0 g of HATBA (HA tetrabutylammonium) were dissolved in 240 mL of anhydrous DMSO and added with 521 mg of 7-(2-(2-(2-iodoethoxy)ethoxy)ethoxy)-2H-chromen-2-one (prepared as reported in Example 3 WO2014122580). The reaction proceeds for 48 hours at 40° C.; a saturated solution of NaBr is then added under stirring, therefore precipitation is effected by adding EtOH. The product is purified by washing in EtOH/H$_2$O 95:5 and absolute EtOH, then dried under high vacuum. The product thus obtained is analyzed by FT-IR, RP-HPLC and 1H NMR, exhibiting a functionalization equal to 32% and a yield of 92%.

Example 2: Synthesis of the Linker Umbelliferone-TEG-Amine to be Bonded to HA or Gelatin Through Amide Bond (2 Steps)

Step 1 of 2: t-butyl (2-(2-(2-((2-oxo-2H-chromen-7-il)oxy)ethoxy) ethoxy)ethyl)carbamate synthesis Into a two-necked flask equipped with magnetic stirring, nitrogen flow, oil bath and coolant, umbelliferone (221 mg), K$_2$CO$_3$ (0.94 g; 5 eq) and anhydrous acetone (10 mL) are introduced, followed by 18-crown-6 in catalytic amount (0.01 eq), then N-BOC 2-[(2-p-tosyloxyethoxy)ethoxy]ethylamine (0.49 g; 0.85 eq). The reaction is left to proceed to reflux under stirring for 48 hours. The reaction mixture cooled through a Gooch funnel is filtered and acetone is removed at low pressure. It is recovered with DCM (dichloromethane), and extracted with H$_2$O:NaHCO$_3$ $_{(sat)}$ 1:1. The organic phase, passed over MgSO$_4$·12H$_2$O, is dried on rotavapor and mechanical pump. 1H NMR and HPLC-MS analyses confirm the formation of the desired product in the form of yellowish-brown oil (0.50 g; yield: 94%).

Step 2 of 2: 7-(2-(2-(2-amminoethoxy)ethoxy) ethoxy)-2H-chromen-2-one synthesis

In a two-necked flask, containing t-butyl (2-(2-(2-((2-oxo-2H-chromen-7-il)oxy)ethoxy)ethoxy)ethyl)carbamate (0.50 g), an anhydrous atmosphere is created. Then DCM (10 mL), Milli-Q® water (200 μL) (distilled or double-distilled water), followed by TFA (trifluoroacetic acid—20.0 mL) are introduced, and the reaction is left to proceed under stirring, at room temperature, for 3 hours. Solvent is removed through rotavapor, recovering three times with DCM, then it is dried on rotavapor and in mechanical pump for one night. An HPLC-MS analysis confirms the nature of the desired product, with chromatographic purity of 95%.

Example 3: Synthesis of the HA-TEG-Umbelliferone Conjugate Through Amide Bond from HANa MW 200 kDa In a two-necked flask equipped with magnetic stirrer and nitrogen flow, HANa 200 kDa (1.20 g; 2.99 mmol) is dissolved in 40 mL of MES (2-(N-morpholino) ethanesulfonic acid) buffer 0.1 M at pH=6, at room temperature. After complete dissolution, 516 mg of N-(3-dimethylaminopropyl)-N-ethyl-carbodiimide hydrochloride (EDC·HCl), 310 mg of N-hydroxysuccinimide and 7-(2-(2-(2-aminoethoxy)ethoxy)ethoxy)-2H-chromen-2-one (pre-dissolved in 10 mL of MES) are added, then the reaction is left to proceed under anhydrous atmosphere at 25° C. for 18 hours. The reaction mixture is dialyzed for 2 days against milli-Q water and it is lyophilized, obtaining 1.496 g of white lyophilizate. The lyophilizate is redissolved in milli-Q water, NaCl$_{(saturated)}$ (¹/₁₀ of the volume of water) is added, it is precipitated with EtOH shaking the solution vigorously. At the end, it is washed with hydroalcoholic mixture EtOH/H$_2$O 9:1, then a final wash with EtOH$_{(abs.)}$. Solvent is removed at low pressure, obtaining the product in the form of white pulverulent solid (1.50 g; quantitative yield). The molar derivatization degree is equal to 10-11% mol/mol (NMR). A titer analysis through HPLC demonstrates the absence of free coumarin.

Example 4: Synthesis of the Conjugate Gelatin-TEG-Umbelliferone

In a 100 mL two-necked flask equipped with magnetic stirrer and glycol bath, 60 mL of PBS (phosphate buffer solution) 0.01 M, pH=7.4 and 1.2 g of bovine gelatin are introduced, then temperature is brought to 50° C. for 10 minutes. The reaction mixture is left to cool to 30° C. and it is degassed under nitrogen flow for 10 minutes. 0.38 g of N-(3-dimethylaminopropil)-N-ethyl-carbodiimide hydrochloride (EDC·HCl), 0.23 g of N-hydroxysuccinimide and 1.30 g of 7-(2-(2-(2-aminoethoxy)ethoxy)ethoxy)-2H-chromen-2-one are added, maintaining the pH of the solution between 5 and 6. It is left to proceed under stirring at 30° C. for 24 hours. The reaction mixture is filtered through 0.45 μm RC (regenerated cellulose), then it is dialyzed for 2 days against Milli-Q® water. Finally, it is lyophilized, obtaining a white-yellowish lyophilizate (0.74 g, yield: 57%). The degree of molar substitution, calculated by UV, resulted to be 28%.

Example 5: Synthesis of the Linker Umbelliferone-Octylamine to be Bonded to HA Through Amide Bond

Step 1 of 2: tert-butyl (8-((2-oxo-2H-chromen-7-il)oxy)octyl) carbamate synthesis In a two-necked flask equipped with magnetic stirrer, nitrogen flow, oil bath and coolant, umbelliferone (221 mg), $K_2CO_3$ (0.94 g; 5 eq) and anhydrous acetone (10 mL) are introduced, followed by 18-crown-6 in catalytic amount (0.01 eq), then 8-((tert-butoxycarbonyl)amino)octyl 4-methylbenzenesulfonate (0.49 g; 0.85 eq). The reaction is left to proceed to reflux under stirring for 48 hours. The reaction mixture cooled through a Gooch funnel is filtered and acetone is removed at low pressure. It is recovered with DCM, and it is extracted with $H_2O:NaHCO_{3(sat)}$ 1:1. The organic phase, passed over $MgSO_4·12H_2O$, is dried on rotavapor and mechanical pump. 1H NMR and HPLC-MS analyses confirm the formation of the desired product in the form of yellowish-brown oil (0.50 g; yield: 94%).

Step 2 of 2: 7-((8-aminooctyl)oxy)-2H-chromen-2-one synthesis

In a two-necked flask, containing tert-butyl (8-((2-oxo-2H-chromen-7-il)oxy)octyl) carbamate (0.50 g), an anhydrous atmosphere is created. Then DCM (10 mL), milli-Q (200 μL) water, followed by TFA (20.0 mL) are introduced, and reaction is left to proceed under stirring, at room temperature, for 3 hours. Solvent is removed through rotavapor, recovering three times with DCM, then it is dried on rotavapor and in mechanical pump for one night. An HPLC-MS analysis confirms the nature of the desired product, with chromatographic purity of 96%.

Example 6: Synthesis of HA-Octyl-Umbelliferone from HANa 200 kDa

In a two-necked flask equipped with magnetic stirrer and nitrogen flow, HANa 200 kDa (1.20 g; 2.99 mmol) is dissolved in 40 mL of MES buffer 0.1 M at pH=6, at room temperature. After complete dissolution, 516 mg of N-(3-dimethylaminopropil)-N-ethyl-carbodiimide hydrochloride (EDC·HCl), 310 mg of N-hydroxysuccinimide and 7-(2-(2-(2-aminoethoxy)ethoxy)ethoxy)-2H-chromen-2-one (pre-dissolved in 10 mL of MES) are added, then the reaction is left to proceed in anhydrous atmosphere at 25° C. for 18 hours. The reaction mixture is dialyzed for 2 days against milli-Q water and it is lyophilized, obtaining 1.496 g of white lyophilizate. The lyophilizate is redissolved in milli-Q water, $NaCl_{(saturated)}$ (1/10 of the volume of water) is added, it is precipitated with EtOH shaking the solution vigorously. At the end, it is washed with hydroalcoholic mixture (EtOH/$H_2O$ 9:1), then a final wash with $EtOH_{(abs.)}$. Solvent is removed at low pressure, obtaining the product in the form of white pulverulent solid (1.50 g; quantitative yield). The molar derivatization degree is equal to 9.1% mol/mol (GPC-UV), or 10-11% (NMR). A titer analysis through HPLC demonstrates the absence of free coumarin.

Example 6a: Synthesis of HA-Octyl-Umbelliferone from HA-TBA (MW of HA 500 kDa)

In a glass reactor equipped with a thermostatable glycol jacket and magnetic stirring, HA-TBA (2.23 g) and anhydrous DMSO (230 mL) are introduced, then the mixture is left to proceed under stirring at 25° C. until complete dissolution of HA-TBA. Methanesulfonic acid (70 μL) and 1,1'-carbonyldiimidazole (CDI, 58 mg) are then introduced and the mixture is left to proceed under stirring at room temperature for 1 h. Finally, 7-((8-aminooctyl)oxy)-2H-chromen-2-one (1.04 g) prepared as reported in Example 5, pre-dissolved in 20 mL of DMSO, is added and the reaction is left to proceed at 42° ° C. for 42 hours. The mixture is brought to room temperature, then a saline solution of NaBr (28 mL) is added drop by drop under stirring. It is precipitated slowly by adding cool EtOH 96% (500 mL) and it is filtered through Gooch. The precipitate is washed with EtOH/water 9:1 hydroalcoholic mixture (×4 times) and finally with absolute EtOH, then it is dried under high vacuum at 40° C. for 3 days. The product is presented in the form of white-yellowish pulverulent solid (1.54 g, quantitative yield). The molar derivatization degree is equal to 11% mol/mol (1H NMR).

Example 6b: Synthesis of HA-Dodecyl-Umbelliferone from HA-TBA (MW of HA 500 kDa)

7-((12-aminododecyl)oxy)-2H-chromen-2-one synthesis: the compound has been synthetized as reported in Example 5, step 1 and 2, replacing 8-((tert-butoxycarbonyl)amino)octyl 4-methylbenzenesulfonate with 12-((tert-butoxycarbonyl) amino)dodecyl 4-methylbenzenesulfonate), with the same stoichiometric ratios.

In a glass reactor equipped with a thermostatable glycol jacket and magnetic stirring, HA-TBA (2.23 g) and anhydrous DMSO (230 mL) are introduced, then the mixture is left to proceed under stirring at 25° C. until complete dissolution of HA-TBA. Methanesulfonic acid (70 μL) and 1,1'-carbonyldiimidazole (CDI, 58 mg) are then introduced and the mixture is left to proceed under stirring at room temperature for 1 hour. Finally 7-((12-aminododecyl)oxy)-2H-chromen-2-one (1.24 g), pre-dissolved in 20 mL of DMSO is added, and the reaction is left to proceed at 42° C. for 42 hours. The mixture is brought to room temperature, then a saturated solution of NaBr (28 mL) is added drop by drop under stirring. It is precipitated slowly by adding cool EtOH 96% (500 mL) and it is filtered through Gooch. The precipitate is washed with EtOH/water 9:1 hydroalcoholic mixture (×4 times) and finally with absolute EtOH, then it is dried under high vacuum at 40° C. for 3 days. The product is presented in the form of white-yellowish pulverulent solid (1.53 g, yield: 97%). The molar derivatization degree is equal to 13% mol/mol (1H NMR).

Example 6c: Gelatin-octyl-umbelliferone Synthesis

Step 1 of 2: Gelatin-TBA Synthesis 60 g of Amberlyst® resin are washed with Milli-Q® water inside a flask leaving the mixture to stand for 5', then filtering through Gooch. The procedure is repeated 4 times. TBA-OH 55% (~180 mL) is added, it is stirred, and it is left to stand for one night at room temperature. Contextually, 5.2 g of gelatin are dissolved in 250 mL of Milli-Q® water, leaving under stirring at room temperature for one night. The resin is washed with approximately 5 L of Milli-Q® water, until the eluate shows pH<10.5 (initial pH=12.84; final pH=10.48), then it is transferred into a 1 L beaker, and the resin/gelatin mix is left to proceed under agitation in water for 24 hours at room temperature. At the end the mixture is filtered through Gooch, rinsing with further Milli-Q® water (200 mL) and leaving under stirring 30' before re-filtrating it again through Gooch. After complete filtration, the pH of the solution is adjusted to 5.0±0.1 by adding HCl 1.0 M, then it is lyophilized. The desired product is obtained in the form of white-yellowish lyophilizate (4.2 g, yield 64%). The product reveals a solubility in DMSO equal to 20 mg/mL at room temperature. An analysis carried out through GPC-SEC-TDA reveals a gelatin-TBA titer equal to 74.1%.

Step 2 of 2: Gelatin-octyl-umbelliferone Synthesis

In a glass reactor equipped with a thermostatable glycol jacket and magnetic stirring, gelatin-TBA (2 g) followed by 200 mL of anhydrous DMSO is introduced, then it is left to dissolve at 80° C. for 30 minutes. After cooling to 42° C., 1,1'-carbonyldiimidazole (CDI, 84 mg) is introduced and the mixture is left to proceed under stirring for 1 h. Then 7-((8-aminooctyl)oxy)-2H-chromen-2-one (0.5 g) prepared as reported in Example 5 is introduced and the reaction is left to proceed under stirring at 42° C. for 42 hours. T is then brought to 20° C., NaBr (saturated) (20 mL) is added drop by drop and it is precipitated adding cool EtOH (600 mL). The precipitate is washed with hydroalcoholic mixture EtOH/water 9:1 (×4 times) and finally with absolute EtOH, then it is dried under high vacuum at 40° C. for 3 days.

The product is presented in the form of white-yellowish pulverulent solid (1.5 g, yield: 89%). The molar derivatization degree is equal to 22% mol/mol (UV).

Example 7: Formulation of Bio-Inks

The bio-inks containing the following components have been formulated:
FID-E: HA-TEG-Umbelliferone ester, prepared as reported in Example 1;
FID-A: HA-TEG-Umbelliferone amide, prepared as reported in Example 3;
GEL: gelatin-TEG-Umbelliferone, prepared as reported in Example 4;
FID-C8: HA-octyl-umbelliferone, prepared as reported in Example 6a.

7.1 Formulation of FID-E 40 mg/mL

In a glass beaker 400 mg of FID-E prepared as reported in Example 1 were weighed; 10 mL of saline solution (NaCl 0.9%) are added and it is left to dissolve under magnetic stirring. After complete dissolution, it is filtered with 0.45 μm cellulose acetate sterile filter.

7.2 Formulation of FID-A 40 mg/mL

In a glass beaker 400 mg of FID-A prepared as reported in Example 3 were weighed; 10 mL of saline solution (NaCl 0.9%) are added and it is left to dissolve under magnetic stirring. After complete dissolution, the solution is transferred in 3 mL glass syringes and it is sterilized by autoclave at 121° ° C. for 15 minutes.

7.3 Formulation of FID-E 40 mg/mL+GEL 20 mg/mL

In a glass beaker 400 mg of FID-E prepared as reported in Example 1 and 200 mg of GEL prepared as reported in Example 4 were weighed; 10 mL of saline solution (NaCl 0.9%) are added and it is left to dissolve under magnetic stirring. After complete dissolution, the solution is heated to 80° C. for 5' and it is filtered with 0.45 μm cellulose acetate sterile filter.

7.4 Formulation of FID-A 40 mg/mL+GEL 20 mg/mL

In a glass beaker 400 mg of FID-A prepared as reported in Example 3 and 200 mg of GEL prepared as reported in Example 4 were weighed; 10 mL of saline solution (NaCl 0.9%) are added and it is left to dissolve under magnetic stirring. After complete dissolution, the solution is transferred in 3 mL glass syringes and it is sterilized by autoclave at 121° C. for 15 minutes.

7.5 Formulation of FID-E 10 mg/mL+HYADD®-4 30 mg/mL

In a glass beaker 100 mg of FID-E prepared as reported in Example 1 were weighed; 10 mL of PBS pH 7.0 are added and it is left to dissolve under magnetic stirring. After complete dissolution, the 10 mL are transferred to a 50 mL Falcon tube, 300 mg of HYADD®-4 are added and it is placed in the stove at 80° C. for 2 hours, mixing with a spatula approximately every 20'. After pre-heating is completed, it is filtered on a 0.5 mm pre-filter and it is divided in 3 mL glass syringes and it is sterilized by autoclave at 121° C. for 15 minutes.

7.6 Formulation of FID-E 10 mg/mL+HYADD®-4 40 mg/mL

In a glass beaker 100 mg of FID-E prepared as reported in Example 1 were weighed; 10 mL of PBS pH 7.0 are added and it is left to dissolve under magnetic stirring. After complete dissolution, the 10 mL are transferred to a 50 mL Falcon tube, 400 mg of HYADD®-4 are added and it is placed in the stove at 80° C. for 2 hours, mixing with a spatula approximately every 20'. After pre-heating is completed, it is filtered on a 0.5 mm pre-filter and it is divided in 3 mL glass syringes and it is sterilized by autoclave at 121° C. for 15 minutes.

7.7 Formulation of FID-E 10 mg/mL+HBC 30 mg/mL

In a glass beaker 100 mg of FID-E prepared as reported in Example 1 were weighed; 10 mL of PBS pH 7.0 and are added and it is left to dissolve under magnetic stirring. After complete dissolution, the 10 mL are transferred to a 50 mL Falcon tube, 300 mg of HBC are added and it is placed in the stove at 80° C. for 2 hours, mixing with a spatula approximately every 20'. After pre-heating is completed, it is filtered on a 0.5 mm pre-filter and it is divided in 3 mL glass syringes and it is sterilized by autoclave at 121° ° C. for 15 minutes.

7.8 Formulation of FID-E 10 mg/mL+HBC 40 mg/mL

In a glass beaker 100 mg of FID-E prepared as reported in Example 1 were weighed; 10 mL of PBS pH 7.0 are added and it is left to dissolve under magnetic stirring. After complete dissolution, the 10 mL are transferred to a 50 mL Falcon tube, 400 mg of HBC are added and it is placed in the stove at 80° C. for 2 hours, mixing with a spatula approximately every 20'. After pre-heating is completed, it is filtered on a 0.5 mm pre-filter and it is divided in 3 mL glass syringes and it is sterilized by autoclave at 121° C. for 15 minutes.

7.9 Formulation of FID-C8 50 mg/mL

In a 50 mL Falcon tube 1200 mg of FID-C8 prepared as reported in Example 6a are weighed; 24 mL of PBS pH 7.0 are added and it is left to hydrate at room temperature. After approximately 1 hour, the tube is placed in the stove at 60° C., mixing with a spatula approximately every 20'. After pre-heating is completed, it is filtered on a 0.5 mm pre-filter and it is divided in 3 mL glass syringes and it is sterilized by autoclave at 121° ° C. for 15 minutes.

7.10 Formulation of FID-C8 30 mg/mL+GEL 20 mg/mL

In a 50 mL Falcon tube 720 mg of FID-C8 prepared as reported in Ex. 6a and 480 mg of GEL prepared as reported in Ex. 4 are weighed; 24 mL of PBS pH 7.0 are added and it is left to hydrate at room temperature. After approximately 1 hour, the tube is placed in the stove at 80° C., mixing with a spatula approximately every 20'. After pre-heating is completed, it is filtered on a 0.5 mm pre-filter and it is divided in 5 mL glass syringes and it is sterilized by autoclave at 121° C. for 15 minutes.

7.11 Formulation of FID-C8 20 mg/mL+GEL 10 mg/ml

In a 50 mL Falcon tube 480 mg of FID-C8 prepared as reported in Ex. 6a and 240 mg of GEL prepared as reported in Ex. 4 are weighed; 24 mL of PBS pH 7.0 are added and it is left to hydrate at room temperature. After approximately 1 hour, the tube is placed in the stove at 80° C., mixing with a spatula approximately every 20'. After pre-heating is completed, it is filtered on a 0.5 mm pre-filter and it is divided in 3 mL glass syringes and it is sterilized by autoclave at 121° C. for 15 minutes.

7.12 Formulation of FID-A 30 mg/mL+HBC 30 mg/mL

In a 50 mL Falcon tube 900 mg of FID-A prepared as reported in Ex. 3 and 900 mg of HBC powder are weighed; 30 mL of PBS pH 7.0 are added and it is left to dissolve at room temperature in a rotary shaker. After approximately 1 hour, the tube is placed in the stove at 80° C., mixing with a spatula approximately every 20'. After pre-heating is completed, it is filtered on a 0.5 mm pre-filter and it is divided in 3 mL glass syringes and it is sterilized by autoclave at 121° C. for 15 minutes.

7.13 Formulation of FID-A 20 mg/mL+GEL 10 mg/mL+ HBC 30 mg/mL

In a 50 mL Falcon tube 600 mg of FID-A prepared as reported in Ex. 3, 300 mg of GEL prepared as reported in Ex. 4 and 900 mg of HBC powder are weighed; 30 mL of PBS pH 7.0 and are added and it is left to dissolve at room temperature in a rotary shaker. After approximately 1 hour, the tube is placed in the stove at 80° C. for approximately 2 hours, mixing with a spatula approximately every 20'. After pre-heating is completed, it is filtered on a 0.5 mm pre-filter and it is divided in 5 mL glass syringes and it is sterilized by autoclave at 121° C. for 15 minutes.

7.14 Formulation of FID-A 20 mg/mL+GEL 10 mg/mL+ HBC 20 mg/mL

In a 50 mL Falcon tube 600 mg of FID-A prepared as reported in Ex. 3, 300 mg of GEL prepared as reported in Ex. 4 and 600 mg of HBC powder are weighed; 30 mL of PBS pH 7.0 are added and it is left to dissolve at room temperature in a rotary shaker. After approximately 1 hour, the tube is placed in the stove at 80° C. for approximately 2 hours, mixing with a spatula approximately every 20'. After pre-heating is completed, it is filtered on an approximately 0.5 mm pre-filter, it is divided in 3 mL glass syringes and it is sterilized by autoclave at 121° C. for 15 minutes.

The characterization of bio-inks above-described has been done evaluating their pre- and post-crosslinking rheological behavior in order to predict their extrudability and characteristics in the extrusion and post-extrusion phases, and the biologic behavior, i.e. the interaction with cellular species, in particular with cells encapsulated in the bio-ink before the extrusion.

The pre- and post-crosslinking rheological behavior is evaluated by examining different parameters:

dynamic viscosity (n) (pre-crosslinking): a rheometer equipped with a 1° plate/cone system is used, increasing the shear rate (the shear stress) from $0.01\ s^{-1}$ to $2000\ s^{-1}$ at 20° C. and monitoring the dynamic viscosity (n) that in a non-Newtonian fluid decreases with increasing the shear rate. The material's capability to flow after the application of a stress is said shear thinning and it is an essential parameter in order to understand if the material under evaluation has the rheological characteristics of a bio-ink. There is also a direct correlation between the shear thinning and the viability of the cells encapsulated in the bio-ink (Townsend J M et al. *Progress in Polymer Science* 2019, 91:126-140);

yield stress (pre-crosslinking) is defined as the shear stress value above which a material starts to flow and below which it remains static. In other words, if it is possible to measure the yield stress for a material, it is probable that such material, once printed, is capable of maintaining the shape deposited after extrusion for the time necessary for the photoreticulation to occur. For the bio-inks, this type of characteristic is to be preferred to a high viscosity, since a material with yield stress does not deform over time, differently from a high viscosity material;

viscoelastic moduli (post-crosslinking): the viscoelastic moduli (G': viscoelastic modulus; G": viscose modulus) are used on the hydrogel formed after crosslinking following UV irradiation in order to confirm the capability of the hydrogel to polymerize forming a compact structure and capable of maintaining its own shape.

Pre-Crosslinking

The tested mixtures, in the shape of hydrogel, are:

FID-E+HYADD®-4 as reported in Example 7.6;

FID-E+GEL as reported in Example 7.3.

The respective concentrations are also reported for convenience in the legends of the graphs represented in the FIGS. 4-7 attached.

The evaluation was done with an Anton Paar RheoCompass rheometer, equipped with a 1° plate/cone system, increasing the shear rate from $0.01\ s^{-1}$ to $2000\ s^{-1}$ and monitoring the dynamic viscosity (n) at 20° ° C., expressed in Pas·sec.

The values obtained for the tested mixtures are related to the corresponding values of *Nivea creme*, "gold standard" of printing (Paxton N et al. *Biofabrication* 2017, 9, 044107) and of a commercial ink (Cellink Start).

The graphs reported in FIG. 1 highlight that all the tested mixture have a shear thinning behavior.

Yield Stress: for the mixtures under evaluation, the yield stress values were measured with a rheometer equipped with a 1° plate/cone system, increasing the shear stress from 0.01 Pa to 1000 Pa at 25° C., and are summarized in the following

TABLE 1

| Sample | FID119-E | HYADD ®-4 | GEL | Yield Stress (Pa) |
|---|---|---|---|---|
| Nivea Creme | — | — | — | 80 |
| FID-E + HYADD ®-4 | 10 | 40 | — | 73 |
| FID-E + GEL | 40 | — | 20 | 61 |

The measured yield stress values, very close to those of *Nivea creme*, further confirm that the tested mixtures are suitable for the applications according to the present invention.

Comparable results have been obtained, under the same conditions, also for the formulation of FID-A+GEL prepared as reported in Example 7.4, whose dynamic viscosity values are reported in FIG. 2.

Post-Crosslinking

The hydrogels FID-E (as reported in Example 7.1) and FID-A (as reported in Example 7.2) have been UV irradiated ($\lambda_{max}$: 365 nm) for 30 s at PWR 100 (Dymax BlueWave QX4; output intensity 13.9 W/cm$^2$, no focusing lens). Viscose and elastic moduli (G'; G'') have been evaluated with Anton Paar RheoCompass rheometer equipped with parallel plate/plate (gap 0.3 mm, strain 10% and @ from 0.1 to 100 rad/s). The graph reported in FIG. 3 demonstrates that the solution-gel transition happens, resulting in the formation of compact and solid structures. The same experiment repeated for FID-E+HYADD®-4 demonstrates that, as expected, the addition of a further derivate of HA improves significantly the post-crosslinking rheological properties (FIG. 4).

Figure 7:
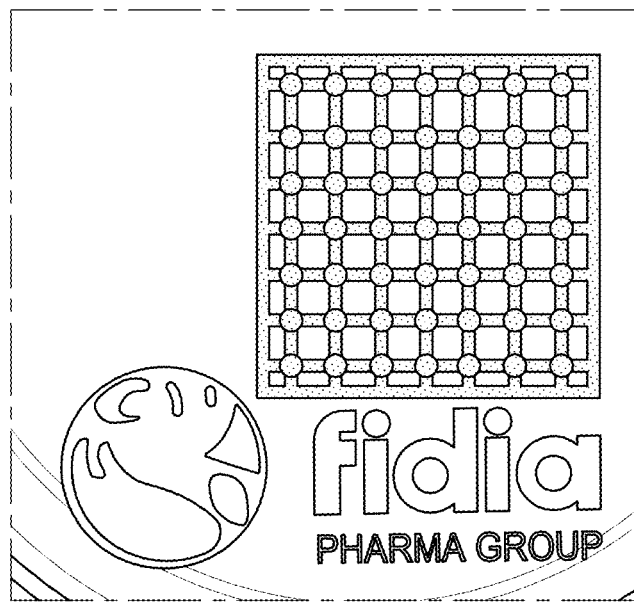
FIG. 7 illustrates the printed and crosslinked lattice with a total of four layers as set forth in Example 7.

To confirm that the viscoelastic characteristics of the tested hydrogels are suitable to the applications according to the present invention, a printing proof has been executed, described below:

3 mL of formulate FID-E+HYADD®-4 prepared as reported in Example 7.6 have been transferred in a cartridge for 3D printer (BIO X™—Cellink) and a lattice sized 3×3 cm (FIG. 5) was printed; at the end of the deposition of each layer (layer) the material has been irradiated at 365 nm for 15 seconds (FIG. 6), before deposing the next layer. The print is considered completed after the deposition of a total of 4 layers. When the process was completed, a compact, manageable lattice and which is capable of stably maintaining the shape acquired after irradiation was obtained (FIG. 7).

The biological behavior evaluates the in vitro interactions of the hydrogels with cellular species, in terms of post-crosslinking cell viability.

The following were tested:
FID-E: HA-TEG-Umbelliferone ester, formulated as in Ex. 7.1;
FID-A: HA-TEG-Umbelliferone amide, formulated as in Ex. 7.2;

Cell Viability after Encapsulation in Hydrogel and Crosslinking

The cell viability of murine fibroblasts (BALB/3T3 clone A31, ATCC CCL-163) encapsulated in hydrogel of the species under examination was evaluated through in vitro tests at 6 days. The murine fibroblasts were cultured in DMEM medium (Gibco, cat. n. 41965-039, Italy) containing fetal bovine serum 10% (Life Technologies, cat. n. 10270106, Italy) under standard conditions (37° C., 5% $CO_2$) until they reached a confluence of 80%.

The cells were then resuspended at a concentration equal to $7.5 \times 10^5$ cells/mL in solutions of the selected hydrogels; 300 µL of such cellular suspensions ($2.25 \times 10^5$ cells) were pipetted in each well of 24-well Multiwell plates (Sarstedt, cat. n. 83.3922, Germany) and they have been crosslinked for 10 s with UV lamp at 365 nm (DYMAX, USA). Afterwards, 1 mL of DMEM medium containing fetal bovine serum 10% (Life Technologies, cat. n. 10270106, Italy) has been added to each well (Gibco, cat. n. 41965-039, Italy) and plates have been incubated under standard conditions (37° ° C., 5% $CO_2$). The experimental conditions tested were thus divided into three groups:

1) one control group, in which the cells were directly seeded in the well of the plate ($2.25 \times 10^5$ cells);
2) one group in which the cells were encapsulated in FID-E hydrogel, 40 mg/mL;
3) one group in which the cells were encapsulated in FID-A hydrogel, 40 mg/mL.

Each condition was tested in triplicate.

Figure 8:
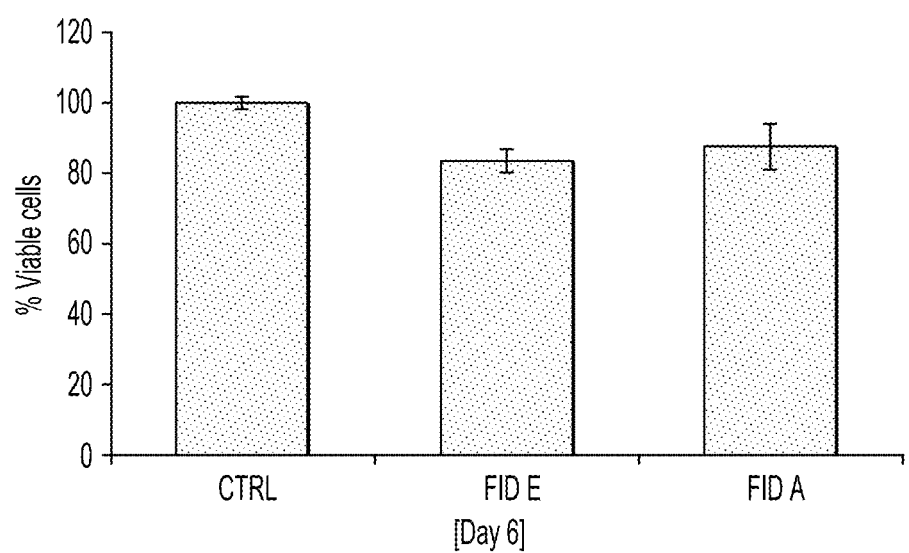
FIG. 8 shows the viability of 3T3 cells after encapsulation as set forth in Example 7.

The day before the predetermined time point the hydrogels were incubated under standard conditions (37° C., 5% $CO_2$) with the enzyme hyaluronidase (52000 UI—Fidia, Italy) in order to dissolve them and to allow the fibroblasts to adhere to the bottom of the well. At the end of the predetermined incubation times, the cell viability was quantified through the Alamar Blue® assay (Life Technologies, cat. n. DAL1025, Italy), according to the instructions given by the manufacturer, in order to determine the mouse fibroblasts' metabolic activity, accomplished at mitochondrial level. The data provided in FIG. 8 have been normalized to the control; from their analysis it is evident that both FID-E and FID-A registered optimal percentage of murine fibroblasts viability after the encapsulation, higher than 80%, with better percentages for the amide derivative (FID-A).

Such result highlights that the encapsulation and cross-linking process of the hydrogels does not compromise the cell viability; the construct obtained for the bio-ink cross-linking according to the present invention is therefore populated by viable cells, thus proliferating, thus capable of acting as a real substitute of living tissue or organ.

The invention claimed is:

1. A method of 3D printing with a bio-ink, said bio-ink comprising a photocrosslinkable conjugate of hyaluronic acid and bifunctional photoreactive linker, or a photocross-linkable conjugate of gelatin and bifunctional photoreactive linker, or mixtures of the two photocrosslinkable conjugates, where the bifunctional photoreactive linker is a coumarin linker, consisting of an umbelliferone residue, bound to a spacer, where, in the photocrosslinkable conjugate of gelatin, the spacer is triethylene glycol, and the linker has the following formula (I):

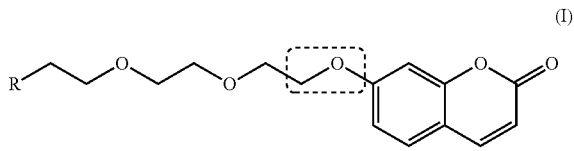

(I)

where:

R=—$NH_2$ for the formation of an amide bond;

or where, in the photocrosslinkable conjugate of hyaluronic acid, the spacer is a linear octyl or dodecyl chain and the linker has the following formula (II):

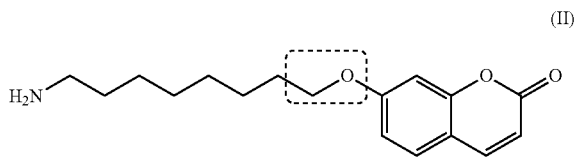 [SMILES: NCCCCCCCCOc1ccc2ccc(=O)oc2c1]

(II)

the bond between bifunctional photoreactive linker and hyaluronic acid or gelatin is an amide bond;

where the hyaluronic acid is produced by and purified from *Streptococcus*, and has a weight average MW comprised between 100,000 and 250,000 Da, or has a weight average MW comprised between 500,000 and 730,000 Da.

2. The method according to claim 1, where gelatin is of Type-B bovine origin and has about 225 g Bloom.

3. The method according to claim 1, said bio-ink further comprising cellular material and/or further components selected from the following hyaluronic acid derivatives hexadecyl amide prepared from a HA with a weight average molecular weight comprised between 500 kDa and 730 kDa, and having an average degree of amidation between 1% and 3% molar;

self-crosslinked internal esters with an esterification percentage between 0.05 and 10%;

crosslinked derivatives, obtained by using crosslinking agents, with a derivatization degree between 5-15% molar, with respect to a repeating unit of the hyaluronic acid, and prepared from HA with weight average MW comprised between 500 and 730 kDa.

4. The method according to claim 1, wherein the bio ink comprises

HA conjugate with a bifunctional photoreactive linker through amide bond, at a concentration ranging from 20 to 60 mg/ml;

gelatin conjugated with the bifunctional photoreactive linker through amide bond, at a concentration ranging from 20 to 60 mg/mL;

mixtures of HA conjugate and gelatin conjugate, wherein a total concentration of the HA conjugate and gelatin conjugate range from 30 to 80 mg/mL, with respect to the above-mentioned total concentration;

mixtures of an HA conjugate or a gelatin conjugate or an HA conjugate and gelatin conjugate mixture, with component a): crosslinked derivatives, obtained by using crosslinking agents, with a derivatization degree between 5 and 15% molar, with respect to a repeating unit of the hyaluronic acid, and prepared from HA with weight average MW comprised between 500 and 730 kDa, component b): hexadecyl amide prepared from a HA with a weight average molecular weight comprised between 500 kDa and 730 kDa, and having an average degree of amidation between 1% and 3% molar, component c): self-crosslinked internal esters with an esterification percentage between 0.05 and 10% or a combination thereof, said component a), component b), component c), or combination thereof being mixed in a ratio ranging from 1:1 to 5:1 with the HA conjugate or with the gelatin conjugate or HA conjugate and gelatin conjugate mixture, a total concentration of components forming the mixtures ranging from 20 to 80 mg/mL.

5. The method according to claim 1, for manufacturing of constructs by 3D printing.

6. The method according to claim 1, wherein the bioink is obtained by polymerization with no photoinitiator.

* * * * *